United States Patent [19]

Matsuzaki et al.

[11] Patent Number: 4,795,604
[45] Date of Patent: Jan. 3, 1989

[54] METHOD FOR MOLDING 1,4,4A,9A-TETRAHYDROANTHRAQUINONE

[75] Inventors: Katsumi Matsuzaki; Kenji Usui; Seishi Ikemoto, all of Kawasaki, Japan

[73] Assignee: Kawasaki Kasei Chemicals Ltd., Tokyo, Japan

[21] Appl. No.: 60,161

[22] Filed: Jun. 10, 1987

[30] Foreign Application Priority Data

Jun. 24, 1986 [JP] Japan .................. 61-146088

[51] Int. Cl.$^4$ .................. B29B 9/04; B29B 9/10
[52] U.S. Cl. .................. 264/144; 264/13; 425/6; 425/310
[58] Field of Search .................. 264/144, 13; 425/6, 425/310

[56] References Cited

U.S. PATENT DOCUMENTS

| | | | |
|---|---|---|---|
| 1,088,741 | 3/1914 | Stephens | 426/634 |
| 1,813,268 | 7/1931 | Bachler | 426/634 |
| 3,221,087 | 11/1965 | Harman | 264/144 |
| 3,405,209 | 10/1968 | Aagaard et al. | 264/144 |
| 3,689,619 | 9/1972 | Borchmann et al. | 264/144 |
| 4,407,840 | 10/1983 | Lathrop et al. | 426/629 |

FOREIGN PATENT DOCUMENTS 54-9256 1/1979 Japan .

Primary Examiner—Philip Anderson
Attorney, Agent, or Firm—Oblon, Fisher, Spivak, McClelland & Maier

[57] ABSTRACT

A method for molding 1,4,4a,9a-tetrahydroanthraquinone by cooling and solidifying a melt of 1,4,4a,9a-tetrahydroanthraquinone, which comprises contacting the melt with a cooling surface of a temperature of from about 50° to about 80° C. for solidification, and peeling off the solidified product.

15 Claims, 1 Drawing Sheet

METHOD FOR MOLDING 1,4,4A,9A-TETRAHYDROANTHRAQUINONE

FIELD OF THE INVENTION

The present invention relates to a method for molding 1,4,4a,9a-tetrahydroanthraquinone.

DISCUSSION OF BACKGROUND 1,4,4a,9a-Tetrahydroanthraquinone (hereinafter referred to simply as THAQ) is a compound which is useful as an intermediate for dyestuffs or as a raw material for anthraquinones and which has recently been used as a pulp digesting agent.

When THAQ is used as a pulp digesting agent, it is common to dissolve it in an aqueous sodium hydroxide solution, and use it in the form of such an aqueous solution. However, for the transportation of THAQ to the users, it is economical to handle it in a solid form.

However, as a result of a study by the present inventors, it has been found that THAQ, for example, a powder of THAQ, is likely to form undesirable lump solid very easily. For instance, when it was packed in bags in an amount of 25 kg per bag, and 10 such bags were piled and stored, whereby THAQ in the bags located at the lower portion of the pile solidified and formed a hard solid. Further, powdery THAQ has a drawback that a dust is likely to form when it is dissolved into an aqueous alkaline solution.

THAQ is usually produced by the Diels-Alder reaction of naphthoquinone (meant for 1,4-naphthoquinone unless otherwise specified) with butadiene (meant for 1,3-butadiene unless otherwise specified). However, it is chemically unstable such that it is susceptible to dehydrogenation by air or by light, or to enolization in the presence of a certain amount of an acid or base component to form 1,4-dihydroanthrahydroquinone or 1,4-dihydroanthraquinone. This tendency is particularly distinct in the case of THAQ obtained by using naphthoquinone for industrial purposes, as the raw material. Accordingly, in order to store or handle THAQ under a stabilized condition, it is preferred to mold it into pellets. For a molding method of THAQ, a patent application has been filed (Japanese Unexamined Patent Publication No. 9256/1979) for a method for molding by means of a flaker. However, in the method disclosed in this patent publication, particularly in the Examples thereof, the Diels-Alder reaction is conducted usually in the presence of an inert solvent such as o-xylene, and the method has a disadvantage such that unless the solvent is removed almost completely, for example, to a level of at most 0.1% by weight, from the reaction solution containing THAQ, the product is hardly moldable. Further, the solidification speed of the melt of THAQ, and the releasability of the molded product have been inadequate. Thus, with such a method alone, it has been practically difficult to practice the method on an industrial scale.

SUMMARY OF INVENTION

The present inventors have conducted extensive researches with an aim to solve the drawbacks of the above-mentioned conventional methods, and as a result, have found that when a melt of THAQ obtained by reacting naphthoquinone with butadiene in an inert solvent and distilling the solvent off the reaction solution composed mainly of THAQ under reduced pressure, is contacted with a cooling surface for cooling and solidification, if the melt is cooled and solidified on a cooling surface of a temperature higher than the temperature range of from 41° to 43° C. of the cooling surface of the above-mentioned prior art, the molding can be conducted very easily with improved releasability of the molded product, and further that if the melt of THAQ is first cooled and solidified at a temperature of lower than about 50° C., and then the temperature of the cooling surface is raised to a temperature of about 60° C. or higher, it is possible to readily mold the melt of THAQ which is otherwise hardly moldable (this is particularly preferred in a case where the melting point of the resulting THAQ is relatively low). The present invention has been accomplished on the basis of these discoveries.

Firstly, the present invention provides a method for molding 1,4,4a,9a-tetrahydroanthraquinone by cooling and solidifying a melt of 1,4,4a,9a-tetrahydroanthraquinone, which comprises contacting the melt with a cooling surface of a temperature of from about 50° to about 80° C. for solidification, and peeling off the solidified product.

Secondly, the present invention provides a method for molding 1,4,4a,9a-tetrahydrohydroquinone by cooling and solidifying a melt of 1,4,4a,9a-tetrahydroanthraquinone, which comprises firstly contacting the melt with a cooling surface of a temperature of lower than about 50° C. and higher than about 40° C. for solidification, then heating the cooling surface to a temperature of from about 50° to about 80° C., and peeling off the solidified product.

DETAILED DESCRIPTION OF THE PREFERRED EMBODIMENTS

Figure 1:
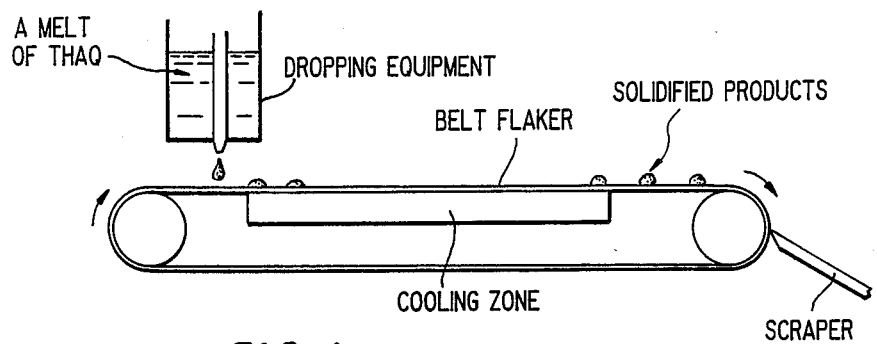
FIG. 1 shows the stainless belt flaker used in Example 1 of the present specification.
Figure 2:
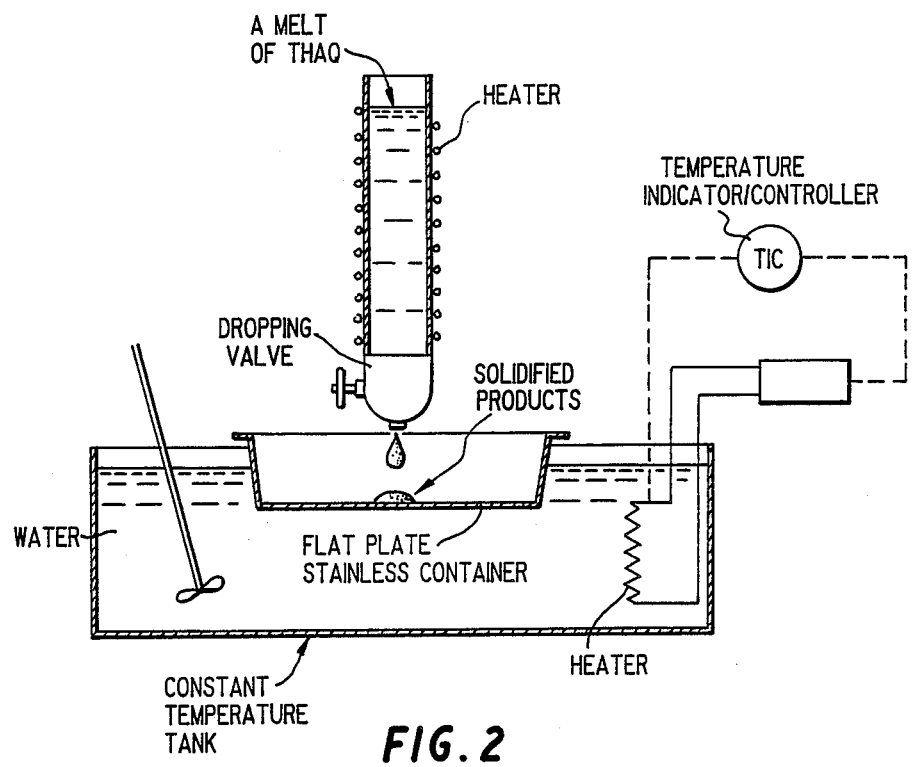
FIG. 2 shows the apparatus used in Examples 2 and 3 of the present specification.

In the present invention, THAQ is produced by the Diels-Alder reaction of naphthoquinone with butadiene. As the naphthoquinone raw material, it is usual to employ a material of industrial grade. As the naphthoquinone to be used in the present invention, it is preferred to use highly pure naphthoquinone obtained by removing impurities completely. However, such a highly pure material is expensive, and it is usual to employ naphthoquinone for industrial purposes. The naphthoquinone for industrial purposes is obtained usually by separating it, for instance by a wet collection by means of an aqueous medium, from a reaction product gas obtained by a catalytic vapor phase oxidation reaction of naphthalene and containing naphthoquinone, phthalic anhydride and naphthalene. For example, the reaction product gas from the catalytic vapor phase oxidation of naphthalene is washed with water or with an aqueous medium containing maleic acid or phthalic acid to obtain an aqueous slurry of naphthoquinone and phthalic acid, which is then heated to dissolve phthalic acid in water, and then substantially naphthoquinone only is extracted with an inert organic solvent e.g. an aromatic hydrocarbon such as toluene or o-xylene. The naphthoquinone solution thus obtained contains certain amounts of organic acids such as benzoic acid and phthalic acid. Therefore, the solution is washed with a weakly alkaline aqueous solution or with warm water to remove the organic acids. The naphthoquinone solution thus obtained is used for the Diels-Alder reaction with butadiene. The smaller the acid content in the naphthoquinone solution, the better, and the acid content is preferably not higher than 0.1% by weight.

When an inert solvent is used in the present invention, it is preferably a solvent which is inert to the reaction of naphthoquinone with butadiene and which is readily removable by distillation under atmospheric pressure or under reduced pressure at a temperature of not higher than 140° C. For instance, it may be an alcohol such as ethanol or propanol, a chlorinated hydrocarbon such as trichlene or trichloroethane, or an aromatic hydrocarbon such as benzene, toluene, xylene or ethylbenzene. A water soluble solvent is difficult to recover, and for the industrial purpose, it is preferred to employ a lower aromatic hydrocarbon which is water-insoluble and readily removable. Particularly preferred is o-xylene. Namely, naphthoquinone is selectively extracted in the form of an aromatic hydrocarbon solution from the reaction product gas obtained by the catalytic vapor phase oxidation of naphthalene, and the naphthoquinone solution, if necessary after purification, is supplied as a starting material for the Diels-Alder reaction to conduct the reaction with butadiene. Then, the solvent is removed from the reaction solution to a predetermined level, whereby a melt containing THAQ can readily be obtained.

The lower the amount of the solvent remaining in the melt, the better. However, in view of the difficulty in the removal of the solvent, the amount of the remaining solvent is usually not higher than 5% by weight, particularly not higher than 3% by weight from the viewpoint of the moldability and transportation, preferably not higher than 1% by weight.

The Diels-Alder reaction of naphthoquinone with butadiene can be conducted in the absence of a solvent. However, it is usual that the reaction is conducted in the above-mentioned inert organic solvent. The Diels-Alder reaction can be carried out by a conventional method. For instance, to the organic solvent solution of naphthoquinone, a polymerization inhibitor such as t-butylcatechol and butadiene in an amount of at least 1 mol to naphthoquinone, are added, and the mixture is reacted at a temperature of from 90° to 150° C., followed by removal of butadiene. Then, from the reaction solution thus obtained, the solvent is removed to a predetermined solvent content, if necessary, whereby a melt containing THAQ useful for the present invention can readily be obtained.

The melting point of THAQ is usually from about 90° C. to about 100° C. although it is affected by impurities. According to the second aspect of the present invention, even a relatively low melting product can be molded satisfactorily.

As a method for distilling the organic solvent off the THAQ solution, it is usual to employ distillation under atmospheric pressure or under reduced pressure at 140° C., or a method of removing the solvent by steam distillation. The conditions for such a method are suitably determined depending upon the type of the organic solvent used. However, in any case, it is preferred to employ a temperature condition of not higher than 140° C., preferably not higher than 120° C., more preferably not higher than 110° C. and higher than the solidifying temperature, to prevent the enolization of THAQ. To conduct the removal of the solvent as short a period as possible, it may be conducted continuously, for instance, by means of a thin film type evaporating apparatus.

There is no particular restriction as to the molding method in the present invention, so long as the melt of THAQ is contacted with a cooling surface, and the solid product thus formed is peeled off by a scraper (such as a blade or a peeling plate). For example, a molding machine such as a belt-type flaker, table-type flaker or a drum-type flaker, may be employed.

The temperature of the melt of THAQ to be supplied to the molding machine varies depending upon the solvent content in the melt and the purity of THAQ. However, the temperature is usually not higher than about 120° C., preferably at a temperature of from about 90° to about 110° C. The higher the temperature, the more readily the enolization of THAQ tends to proceed. Consequently, the fluidity will be poor, and it is likely that the formed enol closes the nozzle. The lower limit of the temperature is higher than the solidification temperature of the melt so that no problem in the molding operation will be brought about.

The temperature of the cooling surface of the molding machine is usually at least about 50° C. and at most at about 80° C., preferably from about 50° to about 70° C., more preferably from about 50° to about 60° C. If the temperature of the cooling surface is higher than 80° C., it takes a long time for solidification. On the other hand, if the temperature is lower than about 50° C., the melt of THAQ is cooled quickly, whereby the crystals tend to be amorphous, and the melt remains sticky without being solidified, whereby it is likely to stick to the cooling surface and hardly peelable or releasable.

In an industrial operation, it sometimes happens that THAQ undergoes enolization (isomerization) to partially form 1,4-dihydroanthrahydroquinone, or a product containing a substantial amount of impurities i.e. compounds other than those having a anthraquinone nucleus forms. In such a case, the temperature of the cooling surface may be raised to improve the releasability. On the other hand, in such a case, the time for solidification will be prolonged. In a case where such a material is to be treated, firstly, the melt is contacted with a cooling surface of a temperature of lower than about 50° C. for cooling and solidification, then the temperature of the cooling surface is raised to a level of at least about 50° C., preferably from 40° to 80° C., whereby the releasability will be excellent. If the initial cooling temperature is set to be lower than about 40° C., particularly lower than 30° C., the solidification time will be substantially prolonged, such being not preferable. In the case of a product having a relatively high purity, it is unnecessary to employ such a method, but there is no particular disadvantage in employing such a method.

As a method for supplying the melt of THAQ to the cooling surface, it is possible to employ a method wherein the melt is continuously supplied from a nozzle, a method wherein the melt is intermittently supplied to form a certain predetermined shape, or a method wherein the cooling surface is immersed in the melt to have the melt deposited thereon.

The cooling surface is usually cooled by water having its temperature preliminarily adjusted. Of course, it is possible to use other cooling medium.

The retention time for the cooling is suitably selected depending upon the purity of THAQ to be molded, the temperature of the melt and the particle size of the product. It is usually at least about 30 seconds, preferably at least 60 seconds. The cooling time may be long, but the retention for a long period of time is not economical since the apparatus efficiency thereby decreases. Therefore, the shorter the retention time, the better.

A usual manner for the operation of the method of the present invention is as follows. For example, a melt of THAQ having a predetermined temperature is dropped in a predetermined amount at a predetermined interval from a nozzle onto a conveyor type steel cooling surface (such as a belt-flaker) cooled to a predetermined cooling temperature with cooling water, and maintained under cooling for a predetermined period of time, and then the solidified THAQ product is peeled off from the reversed cooling surface by means of a scraper. When the second aspect of the present invention is to be carried out, the portion of the cooling surface at which the melt of THAQ is dropped, is maintained at a temperature of lower than about 50° C., and upon expiration of a predetermined period of time, the temperature of the cooling surface at such a portion is raised to a level of at least about 50° C., whereby the molded product can readily be peeled off.

The present invention provides, for example, the following advantages.

In a molding method wherein the melt of THAQ is directly molded by contacting it with a cooling surface, the cooling time can be shortened as compared with the conventional methods, and the molding can be done with excellent releasability.

Now, the present invention will be described in further detail with reference to Examples. However, it should be understood that the present invention is by no means restricted to such specific Examples.

In this specification, "%" means "% by weight" unless otherwise specified.

EXAMPLE 1

A 60% solution of THAQ was obtained by adding butadiene to a 50% o-xylene solution of naphthoquinone obtained by the catalytic vapor phase oxidation reaction of naphthalene, followed by the Diels-Alder reaction. Ten kg of such a solution was subjected to distillation under reduced pressure at 95° C. under 100 Torr to reduce the content of the solvent to 2.5%. Then, while maintaining the melt at 120° C., 6 kg of the melt thus obtained was droped in an amount of about 0.2 g per drop with an interval of every about 0.4 second onto a stainless belt flaker of 60° C. The belt was moved at a cooling time of about 30 seconds, and the solidified product was peeled off by a scraper at the end. The releasability was extremely good.

The cooling temperature of the cooling surface was changed to 40° C., whereby the melt of THAQ did not sufficiently solidify at the cooling surface, the releasability was poor, leading to the adhesion of the product to the scraper.

EXAMPLE 2

A sample was prepared by adjusting the content of impurities in THAQ. This sample was introduced into a container for supplying a melt of THAQ equipped with a stirrer, a heater and a dropping valve, and a predetermined amount of the melt maintained at a temperature of 120° C. was dropped onto a flat plate stainless container in a constant temperature tank, and the solidification time and releasability were examined. The results are shown in Tables 1 and 2.

TABLE 1

| (Releasability) | | | | |
|---|---|---|---|---|
| Cooling temperature (°C.) | Purity (%) | 97.0 | 95.6 | 93.0 |
| 30 | Releasability | + − | − | − − |
| 40 | | + − | − | − − |
| 50 | | + | + | − |
| 60 | | + | + | + − |
| 70 | | + | + | + |
| 80 | | + | + | + |

Notes: The symbols in the above Table have the following meanings.
+ : Excellent releasability
+ − : Releasable
− : Poor releasability
− − : Not releasable

TABLE 2

| (Solidification rate) | | | | |
|---|---|---|---|---|
| Cooling temperature (°C.) | Purity (%) | 97.0 | 95.6 | 93.0 |
| 30 | Solidification rate (sec.) | 24 | 42 | 56 |
| 40 | | 14 | 32 | 34 |
| 50 | | 11 | 22 | 35 |
| 60 | | 11 | 24 | 41 |
| 70 | | 14 | 32 | 47 |
| 80 | | 18 | 41 | 86 |

EXAMPLE 3

By using the same apparatus as used in Example 2, the melt of THAQ having a purity of 93% which had poor releasability in Example 2, was dropped onto a cooling surface of 40° C. and 50° C., respectively, and after the solidification, the temperature of the cooling surface was heated at a temperature of from 60° to 80° C. for 10 seconds, whereby the releasability of the solidified products were substantially improved, and satisfactory molded product were obtained.

What is claimed is:

1. A method for molding 1,4,4a,9a-tetrahydroanthraquinone by cooling and solidifying a melt of 1,4,4a,-9a-tetrahydroanthraquinone, which comprises contacting the melt with a cooling surface at a temperature of from about 50° to about 80° C. for solidification, and peeling off the solidified product.

2. The method according to claim 1, wherein 1,4,4a,-9a-tetrahydroanthraquinone is obtained by reacting naphthoquinone with butadiene.

3. The method according to claim 1, wherein the melt is obtained by reacting naphthoquinone with butadiene in an inert organic solvent to obtain a reaction solution composed mainly of 1,4,4a,9a-tetrahydroanthraquinone, and distilling the solvent off the reaction solution.

4. The method according to claim 3, wherein the inert organic solvent is a lower aromatic hydrocarbon.

5. The method according to claim 4 wherein the lower aromatic hydrocarbon is benzene, toluene, xylene or ethylbenzene.

6. The method according to claim 5, wherein the xylene is o-xylene.

7. The method according to claim 3, wherein the content of the organic solvent in the melt is not higher than about 5% by weight.

8. The method according to claim 3, wherein the content of the organic solvent in the melt is not higher than 3% by weight.

9. The method according to claim 3, wherein the content of the organic solvent in the melt is not higher than 1%.

10. A method for molding 1,4,4a,9a-tetrohydroanthroquinone by cooling and solidifying a melt of 1,4,4a,9a-tetrahydroanthraquinone, which comprises firstly contacting the melt with a cooling surface of a temperature of lower than about 50° C. and higher than about 40° C. for solidification, then heating the cooling surface to a temperature of from about 50° to about 80° C., and peeling off the solidified product.

11. The method according to claim 1, wherein said cooling surface is at a temperature of about 50°–70° C.

12. The method according to claim 1, wherein said cooling surface is at a temperature of about 50°–60° C.

13. The method according to claim 10, wherein said cooling surface is at a temperature of about 50°–70° C.

14. The method according to claim 10, wherein said cooling surface is at a temperature of about 50°–60° C.

15. The method according to claim 10, wherein after the melt is contacted with a cooling surface, the cooling surface is heated to a temperature of about 60° to 80° C.

* * * * *